(12) United States Patent
Diem et al.

(10) Patent No.: US 6,887,711 B1
(45) Date of Patent: May 3, 2005

(54) METHOD OF CHARACTERIZATION OF BIOLOGICAL ENTITIES

(75) Inventors: Max Diem, Croton-on-Hudson, NY (US); Jill Bargonetti, New York, NY (US); Tamara Gopen, New York, NY (US); Susie Boydston-White, New York, NY (US)

(73) Assignee: Cytospec, Croton-on-Hudson, NY (US)

( * ) Notice: Subject to any disclaimer, the term of this patent is extended or adjusted under 35 U.S.C. 154(b) by 0 days.

(21) Appl. No.: 09/868,463

(22) PCT Filed: Jan. 22, 1999

(86) PCT No.: PCT/US00/01550

§ 371 (c)(1),
(2), (4) Date: Jun. 18, 2001

(87) PCT Pub. No.: WO00/43775

PCT Pub. Date: Jul. 27, 2000

Related U.S. Application Data
(60) Provisional application No. 60/116,755, filed on Jan. 22, 1999.

(51) Int. Cl.[7] .................................................. G01N 33/48
(52) U.S. Cl. ........................... 436/63; 436/94; 436/164; 436/171; 436/172
(58) Field of Search ........................... 436/63, 94, 171, 436/172, 164

(56) References Cited

U.S. PATENT DOCUMENTS

| | | | | |
|---|---|---|---|---|
| 4,999,513 A | * | 3/1991 | Ito et al. | ...................... 250/575 |
| 5,469,375 A | * | 11/1995 | Kosaka | ......................... 702/77 |
| 5,804,448 A | * | 9/1998 | Wang et al. | ................... 436/63 |
| 5,976,885 A | * | 11/1999 | Cohenford et al. | ............ 436/63 |

OTHER PUBLICATIONS

Willard et al., Instruments Methods of Analysis, Sixth Edition, Wadsworth Publishing Company (Belmont, CA), 1981, pp. 8–9.*

* cited by examiner

*Primary Examiner*—Jan M. Ludlow
(74) *Attorney, Agent, or Firm*—Rodney T. Hodgson

(57) ABSTRACT

An apparatus and method are disclosed for measuring the infrared vibrational spectral characteristics of each of a large number of biological entities such as cells, and from the measurements statistically determining the presence of anomalies such as cancer.

33 Claims, 7 Drawing Sheets

METHOD OF CHARACTERIZATION OF BIOLOGICAL ENTITIES

RELATED PATENTS AND APPLICATIONS

This application claims priority from a provisional application 60/116,755 filed Jan. 22, 1999 entitled "A system and method to determine the absence or presence of cancerous disease by infrared spectroscopy", by Diem et al.

FIELD OF THE INVENTION

The field of the invention is the field of infrared spectra of biological entities such as single exfoliated cells from normal and abnormal patients. Differences in such spectra can be used to detect cancer in samples of cells and tissues, and can be used as a screening test.

BACKGROUND OF THE INVENTION

Previous papers and patents claimed to be able to detect the differences between normal and abnormal (pre-cancerous and cancerous) cells and tissue by inspection of the infrared spectra of these cells and tissues. Although some of these patent applications and scientific reports present al least partially valid data, the interpretation of these data mostly lacks the specific understanding of the origin of spectral differences between normal and abnormal cells and tissues.

Early patent applications and scientific reports by Wong and coworkers were based on faulty interpretation of spectral differences in cervical and other cells and tissues. These studies failed to take into account the spectral changes in cells and tissues associated with maturation and differentiation of cells. Since certain cancerous and pre-cancerous diseases are accompanied by disruptions of the regular maturation of cells in tissues, some weak correlation between cancerous disease and spectral features was observed. The inconsistencies of the correlations were blamed on failures of standard methods of cytology and pathology.

Although some of the shortcomings of the earlier patents had been established, U.S. Pat. No. 5,733,739 which amplifies the misinterpretations of earlier reports and patents, and uses data that are clearly misinterpreted, has issued. For example, the patent used infrared (IR) spectral data from extracellular materials, such as mucus, and other confounding factors such as blood cells, for the interpretation of the spectral characteristics of cervical cells. Thus, most data used in their patent are unrelated to actual cancerous and pre-cancerous disease but rather to gross spectral changes due to contamination of cervical cells. The actual spectral changes due to cancerous disease, to be discussed below, cannot be detected by the crude methods described in U.S. Pat. No. 5,733,739.

U.S. Pat. No. 5,596,992 uses infrared spectroscopy to distinguish normal from cancerous leukocytes and other cells by multivariate statistical methods. These studies use highly homogeneous samples and, therefore, have a much higher success in predicting disease from infrared data. However, they have failed to realize a source of spectral heterogeneity that confounds the interpretation of the data, and is due to the stages of cells' reproductive cycle.

We have established that identical and highly pure cells still present spectral heterogeneity due to the differences in their development. Only when cells are separated into homogeneous fractions according to their stage in the cell cycle will homogeneous spectral patterns be observed. Under these circumstances, single cells in one given stage exhibit spectral characteristics that can be directly related to the presence of cancer. Thus, the understanding of the cellular biology underlying the cell's reproductive cycle is necessary for a reliable diagnosis of disease. A method will be reported here that allows the detection of single cells that carry the signature of cancerous disease.

OBJECTS OF THE INVENTION

It is an object of the invention to provide an apparatus and a method for determining characteristics of large numbers of biological entities such as cells.

It is an object of the invention to distinguish normal from abnormal cell populations by statistical analysis of characteristics of a large number of single cells or other entities.

It is an object of the invention to provide an apparatus for measuring the infrared vibrational spectrum of large numbers of single cells or other entities.

It is an object of the invention to provide an apparatus which measures the infrared vibrational spectrum of such a large number of cells or entities that meaningful statistical analysis is possible, in a in a time short enough that the process may be carried out at low cost.

SUMMARY OF THE INVENTION

Apparatus and a method for using the apparatus to determine the infrared vibrational spectral absorption of a large number of individual cells or other biological entities is disclosed. The infrared vibrational spectra characterizing the presence of DNA in the cells is used to determine the statistical proportion of the cells in a non quiescent state, the that proportion is used to determine if the cells represent a cell population having cancerous or other anomalous characteristics.

BRIEF DESCRIPTION OF THE DRAWINGS

FIG. 2A shows a typical infrared absorption spectrum of a protein film. The peaks are referred to by standard nomenclature of vibrations giving rise to the absorptions. FIG. 2B and FIG. 2C show the infrared absorption spectra of DNA and RNA respectively. The horizontal axis (abscissa) describes the wavelength of the infrared radiation, expressed in units of inverse length. The ordinate denotes the amount of light absorbed by a vibration (absorbance) and is presented in arbitrary units. Single cells typically exhibit between 0.05 and 0.2 absorbance units.

In FIG. 5A, the traces of normal and abnormal cells are virtually indistinguishable, indicating that some cells in a sample of abnormal cells maintain normal spectral properties. We attribute these spectral patterns to be associated with inactive (non-dividing) cells of the G0 phase. The spectral traces in FIG. 5B are believed to be due to the G1 phase. The traces due to abnormal cells agree well with those of the G1 trace observed in FIG. 4, trace B, for cancerous ML-1 cells. We believe that the "normal" trace in FIG. 5B differs from the abnormal ones by less DNA spectral contributions. This view is justified by the strong DNA features at 1230 cm$^{-1}$, and the small DNA shoulder at 970 cm$^{-1}$ in the "abnormal" spectra.

DETAILED DESCRIPTION OF THE INVENTION

Scientific Aspects of the Invention a) Aspects of Cellular Biology

Figure 1:
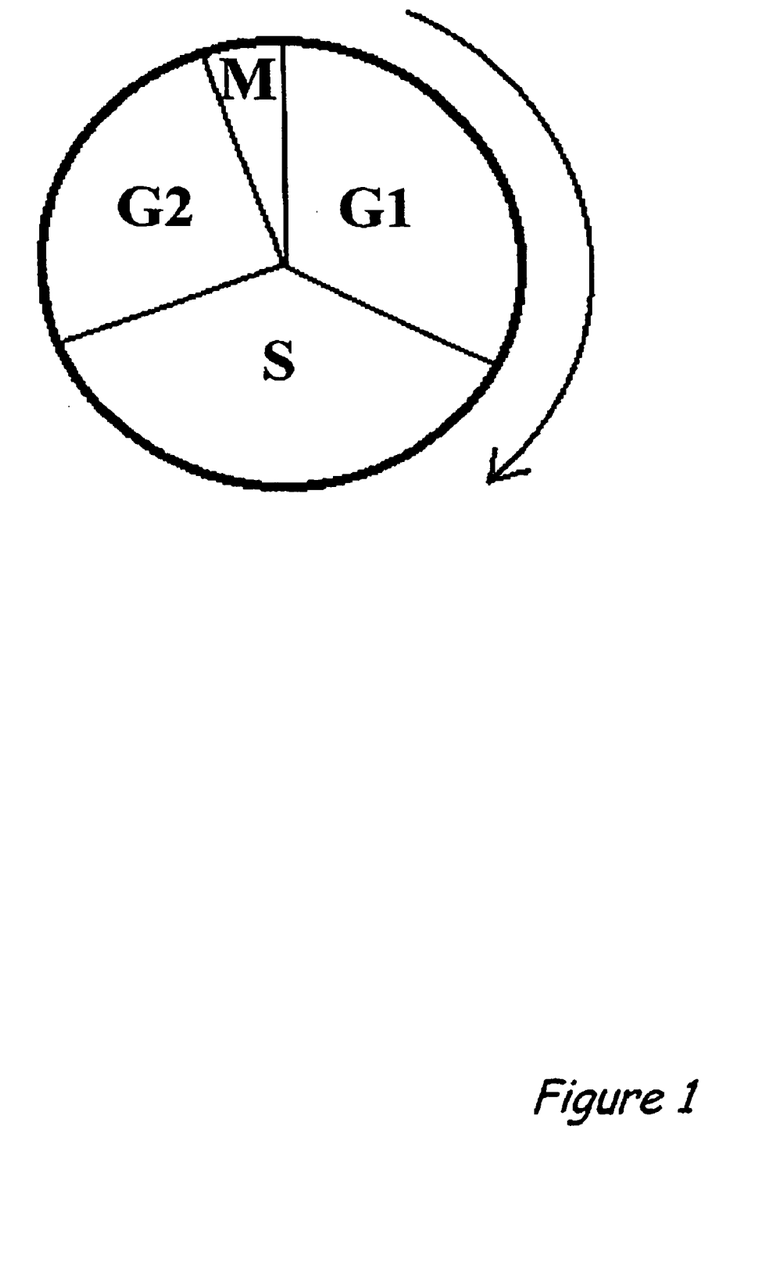
FIG. 1 depicts schematically the stages of the division cycles somatic cells undergo. In cancerous cell cultures, cells often cycle directly from one division cycle into the next; i.e., they are dividing constantly. The width of each slice shown is approximately proportional to the percentage of time the cells spend in a given stage.

Mammalian and other cells undergo division according to a cell cycle scheme depicted in FIG. 1. Normal cells are found predominantly in a state, referred to as G0, in which no reproduction occurs. The division process is initiated by certain biochemical signals, upon which a number of predetermined processes occur that causes a cell to duplicate itself. This duplication process may take 20 to 30 hours, and can be divided into phases Gap 1(G1), Synthesis (S), Gap 2 (G20 and Mitosis (M). In these phases, well-established processes take place: for example, in the S phases, the DNA strands containing the genetic blueprint of the cell are duplicated, whereas in the M phase, the actual cell division takes place; i.e., two new cells are created from the progenitor cell.

Cancerous cells can be cultured indefinitely if the cells are kept at proper conditions for cell growth. In such cell cultures, the cells re-enter the next division cycle as soon as the previous one is completed, and the number of cells doubles after a period of time corresponding in length to the cell division cycle. Such a cell culture is said to be exponentially growing, and the cells found in a given phase of the cycle, i.e. G1, S, G2 and M, is determined by the relative length of these stages, which is about 10 hours for the S phase, 8 hours for G1, 6 hours for G2, and minutes for M.

In order to obtain cells at given stages of their cycles, cultured cells can be separated into fractions of good phase homogeneity by a density/size centrifugation called elutriation. Subsequently, fluorescence activated cell sorting (FACS) technology can be used to identify these fractions as G1, S or G2 phases by the DNA content. These methods present the opportunity to interpret the changes in infrared spectra of cells at various stages of their cell cycles.

b) Aspects of Vibrational Spectroscopy

In infrared spectroscopy, the attenuation of the intensity of a beam of infrared light upon passing through a sample is measured. This attenuation is caused by the interaction of the light with the vibrational transitions of the sample molecules. These absorptions of infrared light, when plotted against the wavelength of the light, produce a unique fingerprint pattern of the molecules encountered by the beam of light. The fingerprint pattern is very useful in identifying entities of biological interest, which include but are not limited to cells, proteins, viruses, fluids, etc. Such fingerprint patterns for a number of cellular components are shown later in this specification. In addition, one can assess the degree of packing of certain cellular components from the infrared spectral patterns: i.e., we have demonstrated before that a nucleus of a quiescent cell is optically so dense that it may not transmit any of the incident infrared radiation, and hence no infrared spectral features due to the cell nucleus are measurable. Consequently, infrared spectroscopy and the appearance of spectral feature due to the nucleus may be used to monitor nuclear processes which result in significant changes in the packing of the constituent molecules.

In infrared microspectroscopy (also referred to as infrared microscopy) the infrared beam is passed through the specimen and focused by an infrared microscope that allows infrared spectral data to be collected from microscopic particles, such as single cells, or pixels of tissue the size of a cell.

The variety of molecules found in a human cell is so staggering that the unambiguous assignment of the infrared spectra of a cell's constituents is not possible, particularly since different proteins, in general, have similar vibrational spectra. However, we and others have shown in the past that changes in molecular composition can be observed and interpreted reliably. For example, different protein/nucleic acid ratios, or the overexpression of structural proteins, can be monitored via infrared microspectroscopy.

c) Aspects of Infrared Spectra of Cells and Tissue

The following section presents a detailed view of recent progress in understanding the infrared spectroscopy of cells and tissues. Such a discussion, and the detailed understanding, has been absent in many of the previous publications and patent applications. Consequently, these earlier efforts were based on intuition, rather than scientific results, and reached unfounded claims and conclusions.

Figure 2:
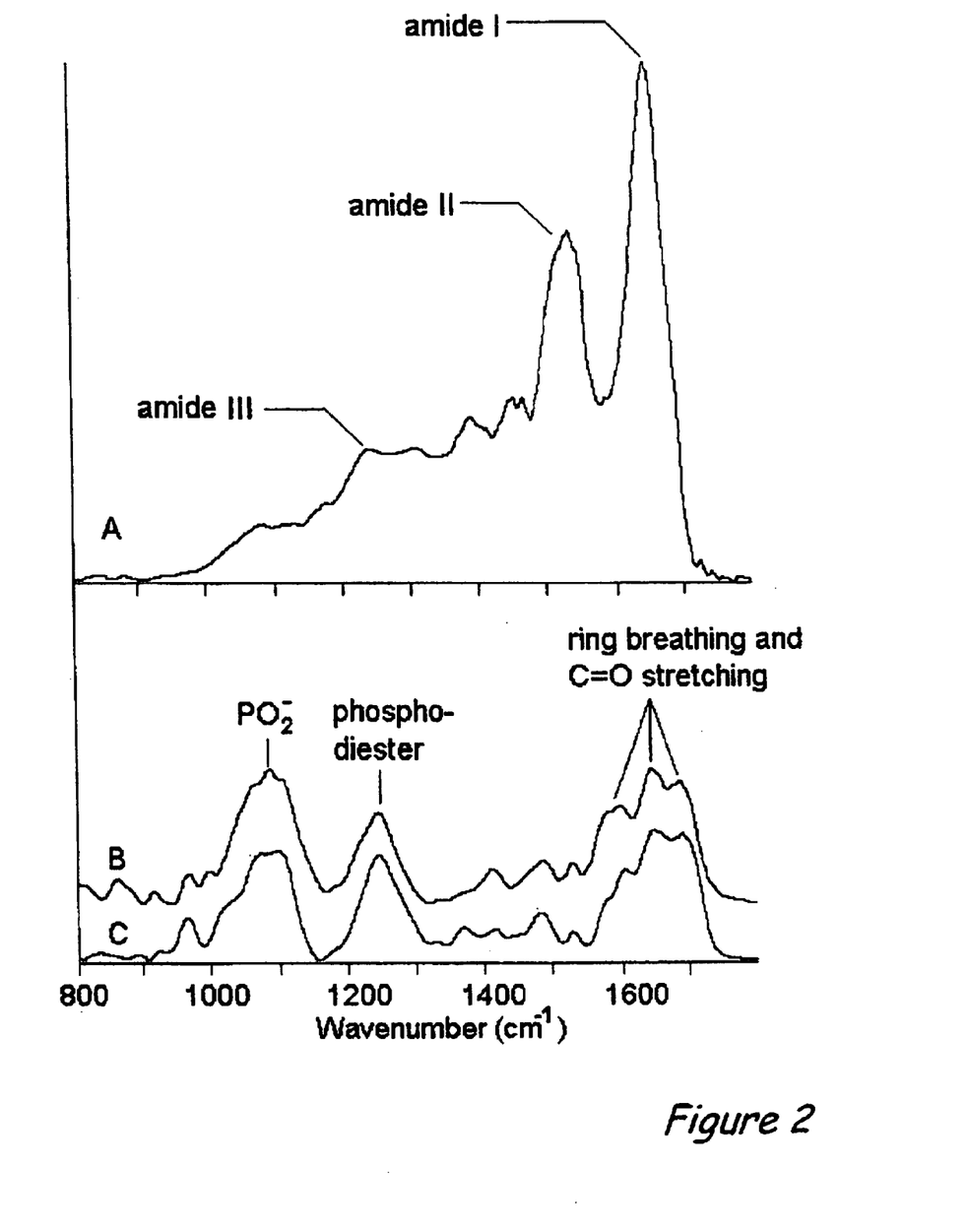

We have found that the infrared spectra of cells and tissues are dominated by the infrared spectral patterns of proteins (as shown in FIG. 2 trace A), which constitute the predominant cellular component by mass. Although there are hundreds or thousands of different proteins in a cell, the protein spectrum observed is determined by the most abundant proteins which generally are structural proteins such as tubuline that determine a cell's overall shape and physical properties.

Protein infrared absorption spectra are known to vary with the secondary structure of the protein (a-helical, pleated sheet, random, etc.), the protein's state of hydration, the solvent's ionic strength, etc. However, the averaged infrared spectra of all metabolic and structural proteins found in cells turn out the be remarkably the same for most cells. The only proteins that exhibit distinctly different spectra are found in connective tissue (e.g., collagen).

The averaged protein spectra found inside cells are dominated by the amide I band at ca. 1650 cm$^{-1}$, the amide II vibration at 1530 cm$^{-1}$, the amide III peak at 1245 cm$^{-1}$, and a number of side chain vibrations in the 1310, 1390 and 1450 cm$^{-1}$ range.

Figure 3:
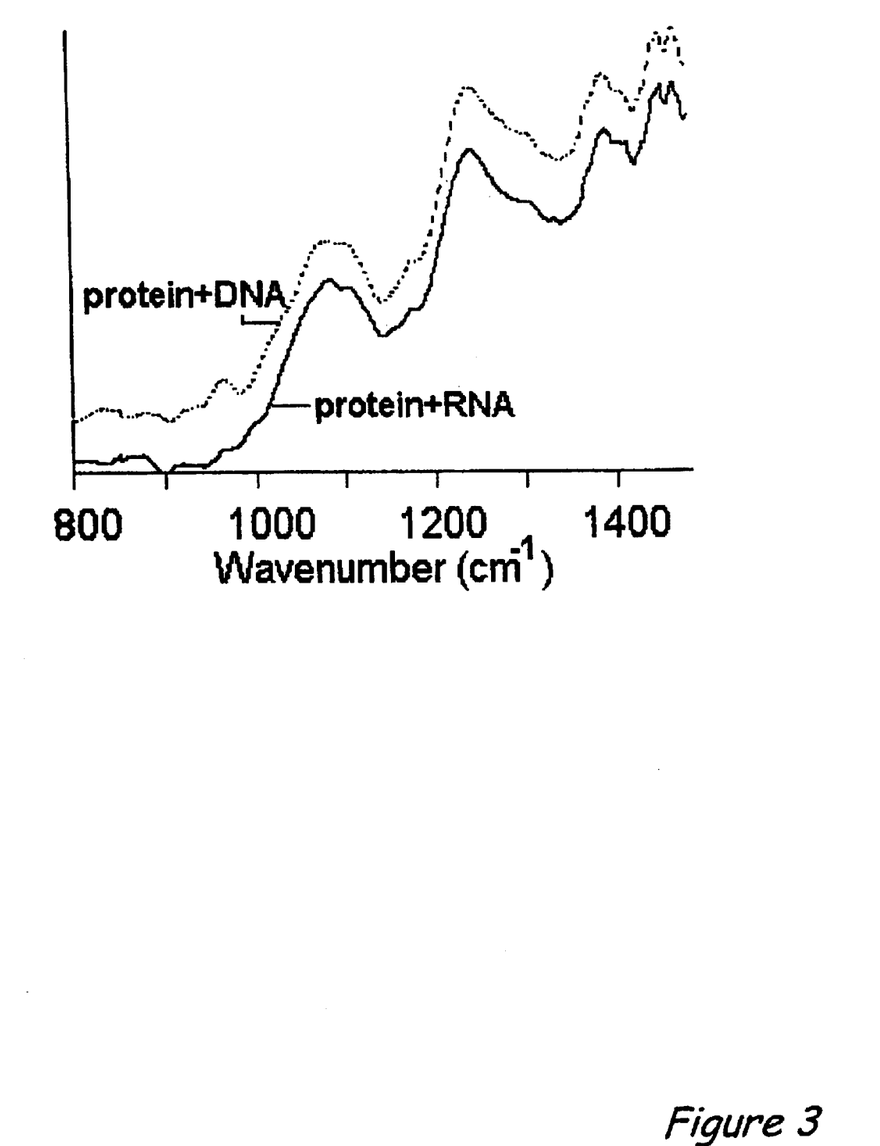
FIG. 3 shows the infrared traces of DNA and RNA, each superimposed on a protein background spectrum. Protein and nucleic acid intensities are adjusted such that their intensities correspond approximately to the intensity ratios observed in cells and tissues. Note that the resulting spectral composites can be easily distinguished; thus, the spectral patterns in FIG. 3 can be used to judge whether DNA or RNA constitutes most of the observable nucleic acid in a cell or tissue.

The infrared absorption spectra of RNA and DNA are shown in FIG. 2, Trace B and C, respectively. These spectra exhibit absorption peaks between 1580 and 1700 cm$^{-1}$ due to the aromatic base breathing and C=O stretching vibrations. The ionized $PO_2^-$ and ribose groups exhibit a triad of peaks that occur in DNA at 1071, 1084 and 1095 cm$^{-1}$ with nearly equal intensities. Further DNA peaks are observed at 965 and 1245 cm$^{-1}$ (the phosphodiester vibration). In RNA, the peak at 1085 cm$^{-1}$ is stronger than the two other peaks in this triad, and forms a distinct "nose". Furthermore, the intensity ratio of this triad to the phosphodiester peak at 1245 cm$^{-1}$ is about 1:0.7, whereas it is about unity in DNA. Since nucleic acid vibrational spectra in cells in tissues are always observed in the presence of protein, we show in FIG. 3 expanded regions of the DNA and RNA spectra superimposed on protein spectra.

In cells, DNA is found in the nucleus and in mitochondria. RNA, on the other hand, can occur in the cytoplasm as ribosomal or transfer RNA (r-RNA and t-RNA), and in the nucleus and cytoplasm as messenger RNA (m-RNA). Thus, the cytoplasm is relatively rich in various RNA species, whereas the nucleus contains nearly all the DNA.

Terminally differentiated, and no longer proliferative cells exhibits virtually no DNA spectral features. Consequently, in these cells mainly the cytoplasmic RNA spectral features are observed superimposed on the protein spectrum. In such cells, the nucleus is very small and very well delimited. The concentration of DNA, RNA and protein in such a nucleus is quite high, and leads to an optical density of the nucleus in excess of 1 absorbance unit. However, DNA is not distributed uniformly throughout the nucleus; rather, it is wrapped tightly around proteins known as histones. Thus, the local concentration of DNA and protein is even higher, and it is likely that the chromosomes of an inactive nucleus will appear as "black" (i.e., opaque or nearly opaque) strings. Little or no spectral information from the DNA can be collected in this case.

Benedetti et al. presented spectral results that confirm this hypothesis. They have observed cells in which there were 64 copies of nuclear DNA whereas in normal cells, there are two copies of DNA. The cells with higher DNA content do not exhibit DNA spectral features stronger than those observed in cells with two copies. Interestingly, with the onset of pre-cancerous and cancerous disease, the DNA signals become generally more pronounced. This aspect, and models to explain it, will be discussed later in this application.

Aside from protein and nucleic acids, carbohydrates (in the form of polymeric sugars or glycoproteins), phospholipids, water, and a few other compounds may occur in cells and tissues at levels that make them detectable via infrared spectroscopy.

d) Aspects of Infrared Spectra at Various Cell Cycle Stages

Even cells of very high homogeneity and purity show significant spectral heterogeneity. This heterogeneity is attributed to the fact that cells may by found at different stages of the reproductive cycle. Healthy and fully mature cells may not divide at all, whereas cells of the proliferative layer of epithelium may undergo slow division. In cancer cells, on the other hand, the division cycle may be a continuous process that leads to a rapid growth of the cancer. Cancerous cells separated according to their reproductive cycle stages (i.e., G1, S, G2 or M) show spectral patterns (FIG. 4) that are distinctly different from the patterns observed in normal samples. Interpretation of these patterns is of prime importance for the understanding of different spectral patterns observed for normal and diseased samples of tissues and cells. As such, the next section is the primary piece of intellectual property to be protected by this disclosure.

Figure 4:
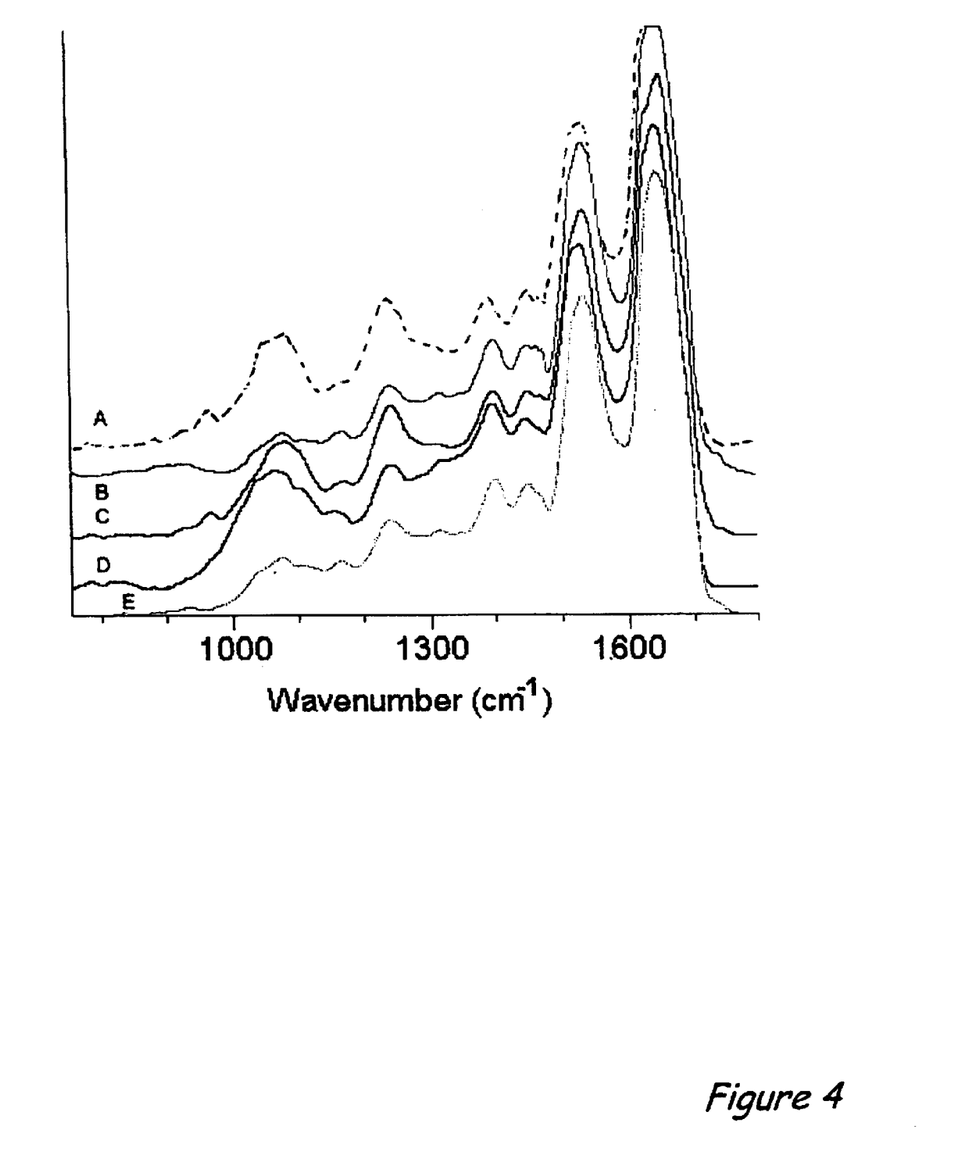
FIG. 4 shows the different spectral traces observed for cultured cells separated into different phases of their division cycle by elutriation. Trace A shows the averaged spectrum obtained for an exponentially growing cell culture, that is, a mixture of all cell division phases. Trace B shows a spectrum for cells in the G1 phase, trace C in the early S phase, trace D in the late S phase and trace E in the G2 phase. Note the differences in the amount of DNA observable between G1 and G2 phase on one hand, and the S phase on the other.

FIG. 4, trace A shows infrared absorption spectra collected from an exponentially growing cell culture of myeloid leukemia (ML-1) cells, and cells fractionated into the cell cycle phases by elutriation. Identification of the cells in a given fraction was performed by fluorescence activated cell sorting (FACS) analysis.

The S phase spectra in FIG. 4 (trace C) resembles that of exponentially growing cells in that it exhibits strong vibrations due to DNA. The spectra of cells in the G1 and G2 phases are similar to each other, and very different from the S phase spectrum in the low frequency region. The shape of the peaks around 1070–100 cm$^{-1}$ (the "nose at 1085 cm$^{-1}$") suggests that in G1 and G2 phases, mostly RNA is observed. The results for cells in the G1 and G2 phases confirmed the hypothesis of opaque DNA: Since cells in the G1 phase are diploid (2 copies of DNA), whereas cells in the G2 phase are quadruploid (4 copies of DNA), one would observe stronger DNA signals if the nuclear DNA was detectable. However, since cells in the G1 and G2 phases exhibit very similar spectral features that bear the signatures of RNA, it follows that the infrared spectra do not detect the DNA in the nucleus, but rather, the cytoplasmic RNA. The strong contributions of DNA in the S phase (Trace C and D), however, are due to the DNA transcription which requires that sections of DNA are unwound from the chromatin, and thus, may become partially transparent to and detectable by IR radiation.

e) Aspects of Spectral Differences Between Normal and Abnormal Samples

When examining healthy and diseased single squamous cells, one observes a mixture of different cells of different stages of maturation. Consequently, one observes a large variety of different spectral traces from these cells. In order to detect spectral changes due to disease, it is advantageous to ignore spectra due to cells that differ by states of maturation or differentiation. This separation can be accomplished by data analysis (vide infra); ie., there is no need to physically separate the cells in the sample.

After all data resulting from different stages of maturity are eliminated from the analysis, one can arrive at a set of spectral traces of cells that are still proliferative. These are the most important for analysis since their progeny cells will carry the same diseased genes. Even among these cells, one detects spectral inhomogeneity that may be attributed to the different phases of the cell cycle. For squamous tissue, for example, the spectral patterns of the immature cells differ significantly between normal and abnormal states of health in some of the observable division phases. However, prior to interpreting these differences in terms of presence or absence of disease, the heterogeneity of the spectral patterns due to the cell's reproductive cycle must be established.

Figure 5A:
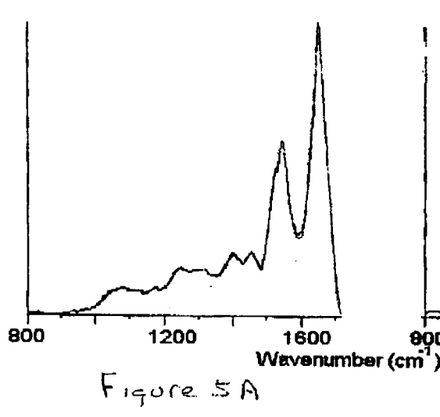
FIGS. 5A and 5B show a comparison between normal and abnormal squamous cells, clustered by cell cycle phase.

The differences between cancerous and non-cancerous cells can be observed most easily in selected cell cycle phases, whereas other phases exhibit virtually indistinguishable traces. FIG. 5A, for example, shows a comparison between healthy and diseased single cell spectra that are virtually superimposable. The low nucleic acid/protein ratio of these spectra suggests that the cells are not dividing actively (G0 or G1 stages). However, reference spectra for the pure G0 phase have not been observed in the ML-1 cells reported above, since they cycle continuously and never reach the inactive phase G0. In normal samples most cells should be found in G0, and even in cancerous cells, the majority of all cells should be in G0.

Figure 5B:
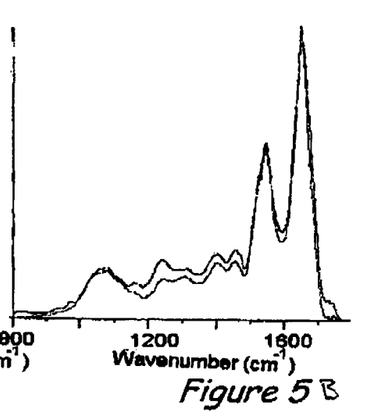

FIG. 5B shows the differences between normal and abnormal cells in a phase whose spectra resemble those observed for the middle of the S phase. The spectra differ enormously in the intensity of the peak at 1230 $cm^{-1}$ to the peak at 1300 $cm^{-1}$. The former of these contains protein and DNA, whereas the latter is nearly a pure protein peak. Thus, any increase of the 1230/1300 $cm^{-1}$ peak intensity ratio is an indication of the visibility of the DNA. This is further confirmed by the appearance of a sharp DNA peak at 970 $cm^{-1}$ in the cancerous samples. Comparing individual spectra from normal and abnormal samples, spectral pairs similar to the ones depicted in FIGS. 5A and 5B can be found. Each spectral pair is thought to arise from a given phase in the cell cycle, and the spectra always differ in the amount of spectral contribution of DNA. This is an indication that normal and cancerous single cells in a number of different stages of their reproductive cycle, can be distinguished by their detectable DNA content.

The intensity ratio of the peaks at 1230/1300 $cm^{-1}$, however, is not a uniformly applicable indicator of disease. We found that any cells actively involved in replication or transcription has a higher visible DNA content than inactive cells. Thus, cell cycle dependent data of cells from various organs need to be collected to create a baseline of how much DNA contribution constitute an abnormality.

The following section describes how the information presented above can be used to screen exfoliated or biopsied cells, tissues or other biological entities for the occurrence of cancer, precancerous aspects, or other biological or physical abnormalities. In particular, the logical steps required to proceed from sample collection to a valid and reliable diagnosis for the most preferred embodiment of the invention will be discussed.

Epithelial cell samples can be derived by scraping the surface of the epithelium with suitable devices such as brushes, spatulas, etc., used presently to collect specimens. Samples from internal organs can be obtained by thin needle aspiration, needle biopsies or surgical biopsies. Cellular components of body fluids (lymphocytes and leukocytes) can be isolated directly from these body fluids. Standard methods, such as digestion with collagenase to break up tissues into individual cells, is utilized to obtain single cells suitable for spectroscopic analysis. Other biological specimens such as proteins and fragments of DNA, RNA, or other molecules may be obtained by methods very well known in the art.

Cells and other biological entities obtained in this fashion are expected to be quite heterogeneous: exfoliated cells, for example, may contain cells at different stages of maturation, whereas lymphocytes and leukocytes may be found at different stages of maturation and differentiation. Cells derived from tissue sections may contain endothelial cells (for example, from blood vessels). This heterogeneity is expected and will not present a significant problem if the spectral data are collected on a cell-by-cell basis, rather than an averaged spectral collection. An earlier patent (e.g., Zakim and Lord, U.S. Pat. No. 5,733,739) reports the use of cell pellets of unknown and variable composition to carry out cancer screening; however, the similarity of spectra of all cells and tissues render such an approach difficult or impossible to implement with any reliability.

The cells or other entities obtained as described above are treated to remove impurities due to blood, lymph, mucus or other confounding constituents. Simple separation procedures are useful to enhance the percentage of desirable entities for the investigation.

The experiments described above reveal that most pronounced differences between normal and abnormal cells are observed when cells replicate their DNA. In fully mature and terminally differentiated cells, this process no longer occurs; thus, it is advantageous to remove them or reduce their numbers.

The collected and purified cells are fixed to prevent degradation of the samples. Flash fixing by ethanol (15 sec, low temperature) produces samples of sufficient stability for spectroscopic analysis. Longer exposure to ethanol may dissolve the cell membranes, may lead to cell fusion and precipitation of cellular components. Subsequently, cells are transferred to one of a number of different infrared transparent substrates for spectral analysis for the most preferred embodiment of the invention.

The spectroscopic sample for the most preferred embodiment consists of a partial layer of cells with good separation between the cells. For the most preferred embodiment of the invention, for example, $10^4$ cells, each occupying about $2 \times 10^{-4}$ $mm^2$ and distributed uniformly on an area of 50 $mm^2$, result in a sample partial layer with an occupation of about 5% of the surface of the substrate. Such a sample is suitable for analysis by the method of the invention, since the infrared absorption spectrum of each cell alone may be recorded. The samples reported by Zakim and Lord often had sample populations 1000–10000 fold higher. The high population creates non-linear absorption effects, retains the solvent in a manner that cannot be controlled, and may be responsible for many of the artifacts reported by them. For the method of the present invention, the spectrum of mostly single entities should be recorded. Overlapping a cancerous with a non cancerous cell, for example, would lead to a spectrum which is not definitive for either type of cell.

Figure 6:
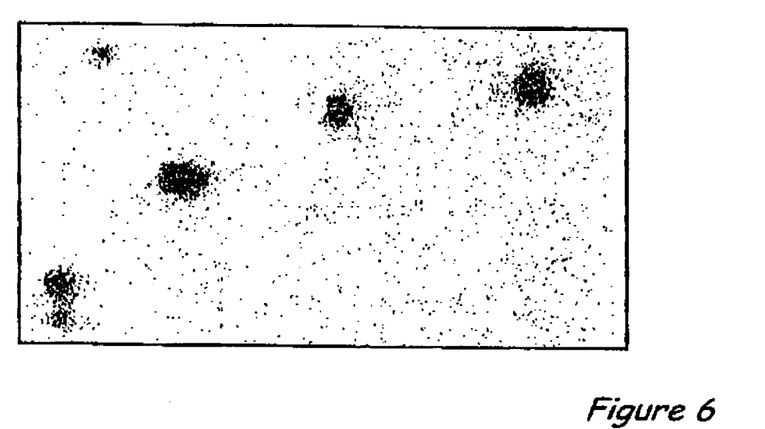
FIG. 6 shows a microscopic image taken of $Eu^{3+}$ stained cells through a fluorescence microscope. The arrow indicates an approximate scale of the display. The figure demonstrates that excellent separation of cells is easily achieved, and that cells can be localized by their fluorescent emission. This localization of cells is used to speed up data manipulation for the infrared imaging, and may serve as indications whether or not single cells are in the field of view of a given infrared detector element.

Cells are most preferably visualized by staining with fluorescent, monatomic dyes (for example, isotonic $Eu^{3+}$ ion solution). Such staining does not perturb the infrared spectra within the limits of detect ability, but permits the cells to be detected using fluorescence excitation. Identification of cells is necessary to avoid data collection from cell debris. An image of a typical cell sample under fluorescence excitation in the most preferred embodiment of the invention is shown in FIG. 6 which demonstrates the excellent separation of cells in this sample preparation procedure.

Figure 7:
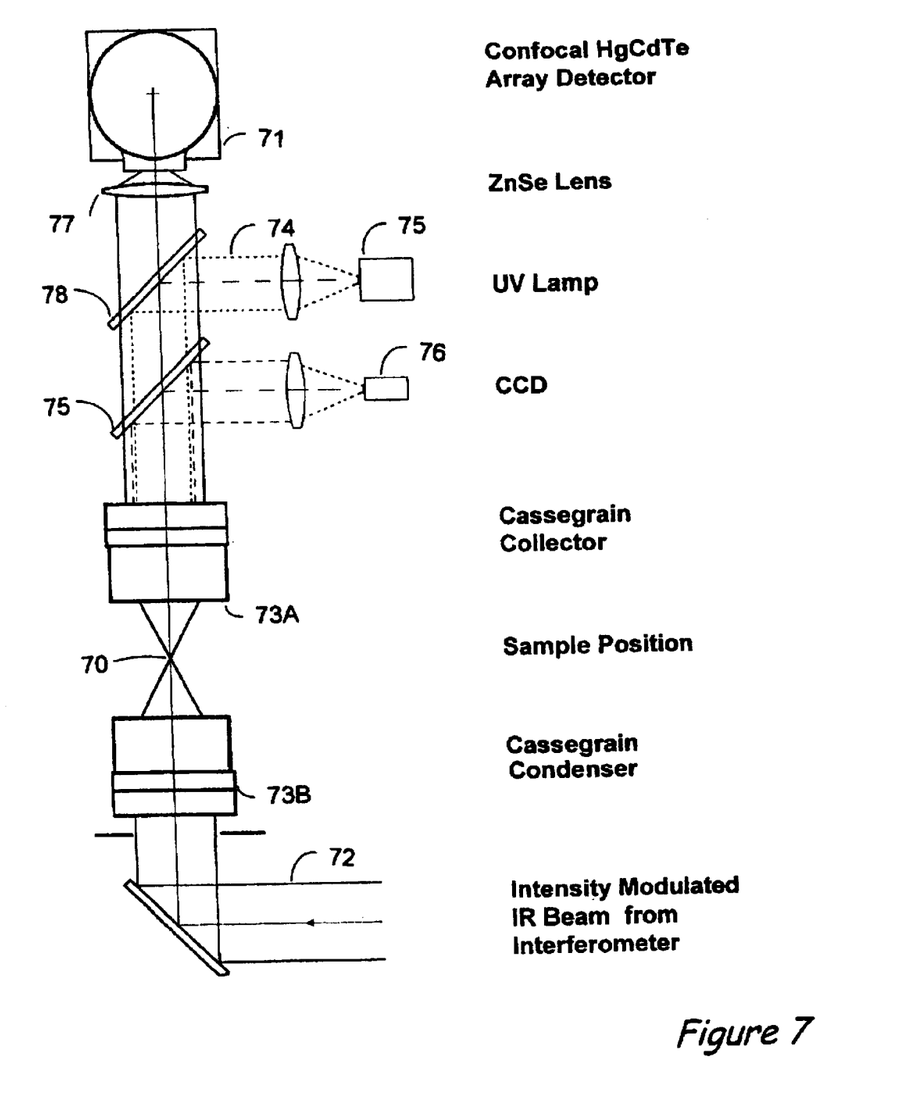
FIG. 7 shows a sketch of the most preferred embodiment of the invention.

The area of the substrate (ca. 50 $mm^2$) that contains the cells is imaged using fluorescent and infrared wavelengths as follows. The substrate is inserted in the focal position 70 of a combination infrared microspectrometer (also known as an infrared microscope) and fluorescence microscope shown schematically in FIG. 7. The infrared microspectrometer is equipped with a confocal, infrared-sensitive array detector 71 of 256×256 (=65536) individual diode elements on an area of about 7×7 $mm^2$. Such instrumentation is commercially available. FIG. 7 shows is the optical arrangement for the infrared/fluorescent microscope combination which is the most preferred embodiment of the invention. Infrared light from the interferometer is passed through a Cassegrain condenser 73A into the sample, collected via an identical Cassegrain objective 73B, and focused with an infrared transmitting lens such as a ZnSe lens 77 onto the confocal array detector 71. Reflecting optics could be used as well in place of the ZnSe lens. In order to reduce computation time for the analysis of up to 10,000 individual cells, only pixels that contain cellular spectral information is processed. This information is obtained by imaging the sample via fluorescence microscopy prior to infrared data acquisition. To this end, the cells are illuminated by introducing an ultraviolet beam of light 74 from a UV lamp 75 into the optical train using a movable mirror 78. The UV light induces intense fluorescence from the cells in the focal region 70 that have been treated with $Eu^{3+}$ ions. Since this stain consists of monatomic ions, it does not exhibit an infrared absorption spectrum; consequently, there is no spectral difference in the infrared spectrum due to stained and unstained cells. The fluorescent light collected in the reflection mode as shown in FIG. 7 is filtered to remove the excitation wavelength by a movable dichroic mirror 75, and is processed via a CCD detector 76. This image taken by the fluorescence light will indicate, by the fluorescent intensities, the position of cells on the sample substrate (cf. FIG. 6). From these positions, one can identify which pixels of the confocal infrared array detector 71 need to be processed to obtain the desired infrared spectral information of the individual cells. Clearly, the UV fluorescent image may equally well be taken in transmission mode, and/or the spectra of the cells may be taken (at less resolution) in reflection mode after reflection from an IR reflecting substrate holding the cells.

The analysis of the cells on the substrate proceeds as follows. The sample substrate is first illuminated with UV light that is absorbed by the $Eu^{3+}$ stain with which the cells have been treated. The fluorescence induced by the UV excitation is observed in reflection mode of the microscope, and collected through selective bandpass filters to reject the excitation wavelength. The fluorescence of the stained cells is detected by the CCD camera, and the positions of all cells on the substrate is computed by the positions of the pixels of the CCD camera detecting the fluorescent radiation.

Subsequently, the illumination of the sample is switched to infrared radiation. The movable mirrors 75 and 78 are removed from the optical path of the microscope and the infrared light is passed through a step-scanning interferometer (not shown) to modulate the wavelength patterns of the light prior to being directed into the microscope. In the alternative, the movable mirror 78 and the dichroic mirror 75 could be formed on IR transparent substrates to reflect the appropriate light and transmit the infrared light. Each of the detector elements of the confocal infrared array detector 71 is exposed to the infrared radiation passing through the sample cells which are imaged 1:1 onto the detector resulting in about 1 cell or less per detector element.

Interferograms are collected for all 65536 detector elements, and converted to infrared absorption spectra via a mathematical process known as Fourier transform (FT). Only the interferograms from detector pixels onto which cells are imaged are Fourier transformed to save data analysis time. These pixels are identified by the fluorescence picture obtained in the previous step. Selecting only picture elements that are known to contain spectral information reduces the number of individual spectra to be calculated from the interferograms from 65000 to between 10,000 and 20,000.

The resulting spectra are uniformly expanded, smoothed and corrected for water vapor absorption. Subsequently, the spectra (or their derivative spectra) are clustered using vector correlation methods. The clustering reveals the degree of "relatedness" of spectral patterns, and will reduce the number of independent observations to a few dozen spectral patterns for each sample. After this clustering, certain spectral traces that are clearly associated with cells of low information content are discarded. For example, spectra from red blood cells or fully mature, inactive cells may be discarded. The resultant spectral patterns, referred henceforth as the "reduced spectral set" is analyzed as follows.

First, the reduced spectral set is compared to the cell cycle dependent reference sets that have been collected beforehand for the organ sample under investigation. This analysis reveals whether or not the distribution of the cell cycle stages falls within normal limits. Subsequently, all spectra in the reduced data set are searched for the occurrence of spectral patterns associated with a fast growing and rapidly dividing cell. The occurrence of such cells in a sample is indicative of abnormality.

The analysis described above requires knowledge of the cellular spectra, and cellular distribution, observed for normal samples. The analysis, however, depends to a lesser degree on bases (reference) sets than the one described by Zakim and Lord, which used spectral averages over large number of cells. It is clear that such an averaging process reduces the sensitivity of the method enormously, since only a small number of cells exhibit spectral traces modified by disease.

The method presented here uses both a statistical analysis of the spectral patterns of the individual cells (i.e., changes in the distribution of cells at various stages of their development), as well as variations in the spectral patterns due to disease, for a vastly enhances sensitivity of the infrared spectral method.

Figure 8:
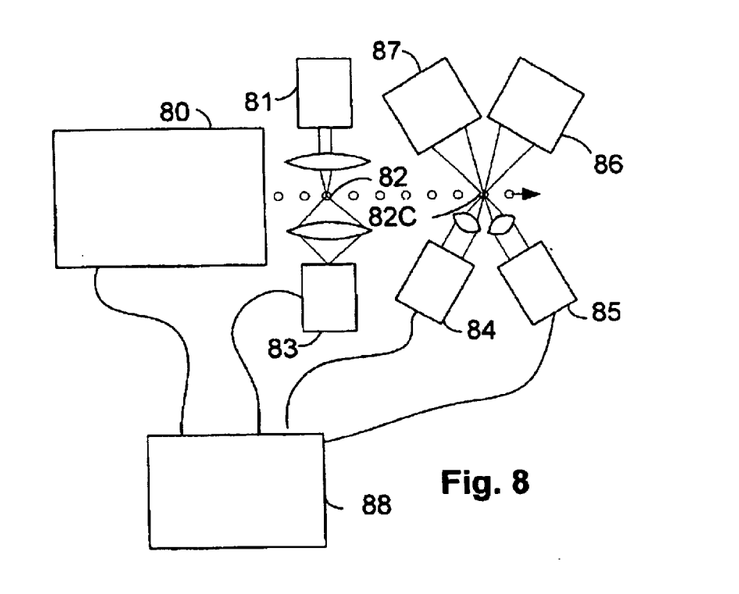
FIG. 8 shows a sketch of a preferred embodiment of the invention.

A preferred embodiment of the invention is sketched in FIG. 8. A specimen generator 80 produces a plurality of specimen 82 in the same fashion as a FACS machine or an ink jet printer. The specimen 82 may be droplets containing the entities to be measured, or may be cells or other biological entities. The specimen are produced and fly through an atmosphere with a defined velocity. The atmosphere may be ordinary laboratory air, or may be air with a controlled water vapor pressure or partial pressure of another vapor such as alcohol, or may be an inert gas such as nitrogen or argon, or vacuum. The specimen are generally electrically charged so that the specimen generator may accelerate them to a relatively high speed. However, such electrical charging is optional. The specimen are optionally marked with a fluorescent marker as detailed above for the marking of cells, and UV light source 81 and fluorescence detector 83 may be used to mark the position of a specimen 82, or indeed may be used to decide whether specimen 82 contains entities to be investigated. The position and speed of each specimen is now known. A vibrational spectrum recording apparatus is now used to record the spectrum of each specimen, and the resulting plurality of spectra is treated as detailed above to characterize the statistics of all the specimen. In the present embodiment, the preferred vibrational spectrum recording device is two infrared light sources 84 and 85 which direct infrared light on to a specimen 82C, and two detectors 86 and 87 which measure the light transmitted through specimen 82C. Light sources 84 and 85 are preferably pulsed laser sources which produce infrared light at frequencies characterizing the infrared absorption spectrum of DNA and RNA respectively. A plurality of such lasers may be used to produce an entire vibrational spectrum for each specimen as detailed in the most preferred embodiment. A computer 88 is shown controlling specimen generator 80 and infrared sources 84 and 85, and monitoring fluorescence detector 83. Lines indicating control and monitor functions for light source 81 and detectors 86 and 87 are not shown to avoid complexity in FIG. 8.

Figure 9:
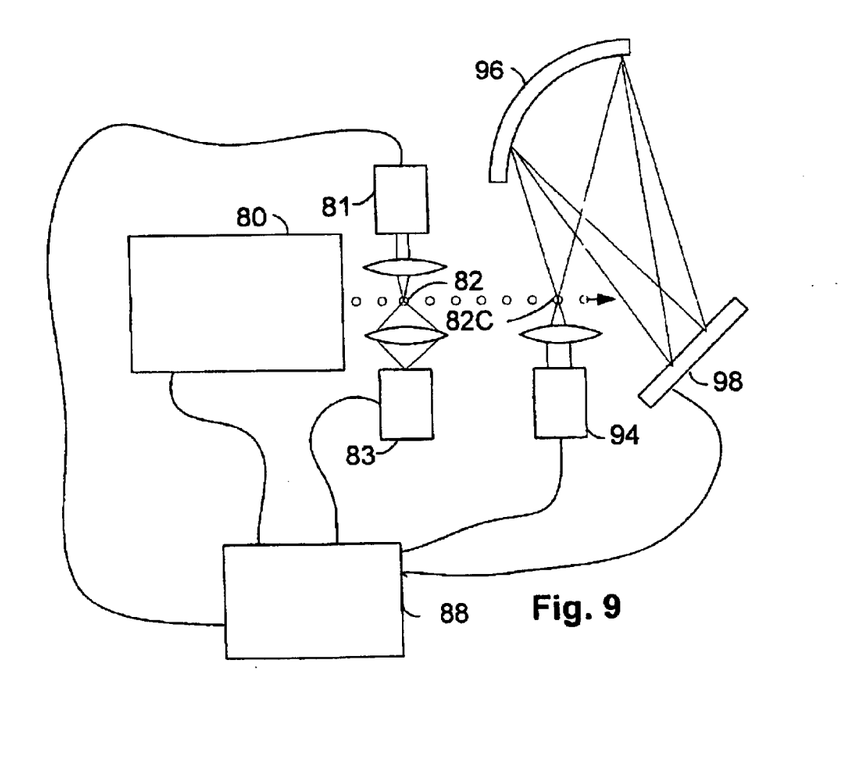
FIG. 9 shows a sketch of a preferred embodiment of the invention.

A preferred embodiment of the invention is shown in FIG. 9, where the separate infrared light sources 84 and 85 are replaced by a broad band infrared light source 94. The infrared light from the source 94 which is preferably a pulsed broad band laser, is focused on a specimen 82C which has been marked as noted above for FIG. 8. The broadband infrared light is then analyzed spectrally as indicated in FIG. 9 by a focusing grating 96 which images light transmitted through the cell onto an array detector 98 according to the infrared wavelength. Rays of two different infrared wavelengths are traced in FIG. 9 in order to guide the eye. The grating 96 could be replaced by an imaging system used to image the light from the specimen 82C on to the slit of a normal spectrometer and infrared recording array detector, or indeed by any other spectral recording device as known in the spectroscopic art.

Lenses conventionally shown in FIGS. 8 and 9 are figurative only, and imaging and light handling devices as known in the art are anticipated by the inventors.

The vibrational spectrum recording devices of the invention are not limited to the devices described above, but may be any vibrational spectrum recording devices known in the spectroscopic art to record IR absorption spectra or Raman spectra.

Obviously, many modifications and variations of the present invention are possible in light of the above teachings. It is therefore to be understood that, withing the scope of the appended claims, the invention may be practiced otherwise then as specifically described.

We claim:

1. A method of characterizing a large plurality of biological cells, comprising:
   a) separating the cells so that the cells of the large plurality are preponderantly separated from each other;
   b) characterizing each cell according to an aspect of the vibrational spectrum of each cell, wherein the vibrational spectrum of each cell is analyzed for indications that the cell is in a cell division stage, and;
   c) statistically analyzing the characteristics of the cells.

2. The method of claim 1, wherein the results of the statistical analysis is the percentage of the cells of the large plurality which are in a cell division stage.

3. The method of claim 2, wherein the indication that a cell is in a cell division stage is the presence of a signal indicating DNA in the vibrational spectrum.

4. The method of claim 3, wherein the separated cells are located according to the fluorescence of the cells.

5. The method of claim 1, wherein the vibrational spectrum of each cell is the recording of an infrared absorption spectrum for each cell.

6. The method of claim 5, wherein the results of the statistical analysis is the percentage of the cells of the large plurality which are in a cell division stage.

7. The method of claim 6, wherein the indication that a cell is in a cell division stage is the presence of a signal indicating DNA in the infrared absorption spectra.

8. The method of claim 7, wherein the separated cells are located according to the fluorescence of the cells.

9. The method of claim 1, wherein the vibrational spectrum of each cell is the recording of a Raman spectrum for each cell.

10. The method of claim 9, wherein the results of the statistical analysis is the percentage of the cells of the large plurality which are in a cell division stage.

11. The method of claim 10, wherein the indication that a cell is in a cell division stage is the presence of a signal indicating DNA in the infrared absorption spectra.

12. The method of claim 11, wherein the separated cells are located according to the fluorescence of the cells.

13. A method, comprising:
   locating a large plurality of separated cells with a location means;
   illuminating the cells with light;
   recording light emitted from the cells; and
   characterizing the vibrational spectrum of the light emitted from each cell located by the location means, wherein the vibrational spectrum is analyzed for indications that the cell is in a cell division stage.

14. The method of claim 13, wherein each cell is illuminated with in infrared light.

15. The method of claim 14, wherein each cell is illuminated using a first laser having a first defined infrared wavelength.

16. The method of claim 15, wherein the first laser is pulsed when the location means locates a first cell in a position to be characterized by the first laser.

17. The method of claim 15, wherein the first defined wavelength comprises a wavelength wherein DNA is highly absorbing.

18. The method of claim 17, wherein a second laser having a second infrared wavelength is pulsed to characterize the cell, wherein the second infrared wavelength comprises a wavelength wherein RNA is highly absorbing.

19. The method of claim 14, wherein each cell is illuminated with infrared light from a third laser having a broad band infrared wavelength range.

20. The method of claim 19, wherein the third laser is pulsed when the location means locates a first cell in a position to be characterized by the laser.

21. The method of claim 20, wherein the broad band infrared wavelength range includes a wavelength wherein DNA is highly absorbing.

22. The method of claim 21, wherein the broad band infrared wavelength range includes a wavelength wherein RNA is highly absorbing.

23. The method of claim 22, wherein the infrared absorption spectrum of each cell is recorded.

24. The method of claim 23, wherein the infrared absorption spectrum of each cell is analyzed for indications that the cell is in a cell division stage.

25. The method of claim 24, wherein the percentage of the cells in the cell division stage is calculated.

26. The method of claim 25, wherein the indication that a cell is in a cell division stage is the presence of a signal indicating DNA in the infrared absorption spectra.

27. The method of claim 13, wherein the location means is a fluorescence activated sorting method.

28. The method of claim 13, wherein the vibrational spectrum is characterized by analyzing the Raman scattered light emitted from the cells.

29. The method of claim 28, wherein cells are illuminated by a first laser having a first defined wavelength.

30. The method of claim 29, wherein the first laser is pulsed when the location means locates a first cell in a position to be illuminated by the first laser.

31. The method of claim 30, wherein the Raman spectrum of each cell is recorded.

32. The method of claim 31, wherein the Raman spectrum of each cell is analyzed for indications that the cell is in a cell division stage.

33. The method of claim 32, wherein the indication that a cell is in a cell division stage is the presence of a signal indicating DNA in the Raman spectra.

* * * * *